(12) United States Patent
Chen et al.

(10) Patent No.: US 8,013,144 B2
(45) Date of Patent: Sep. 6, 2011

(54) HNRNP K EXPRESSION-INHIBITING COMPOUND AND SIRNA SEQUENCE THEREOF

(75) Inventors: Lih-Chyang Chen, Xindian (TW); Yu-Sun Chang, Linkou Township, Taipei County (TW)

(73) Assignee: Chang Gung University, Tao-Yuan (TW)

( * ) Notice: Subject to any disclaimer, the term of this patent is extended or adjusted under 35 U.S.C. 154(b) by 0 days.

(21) Appl. No.: 12/484,823

(22) Filed: Jun. 15, 2009

(65) Prior Publication Data

US 2010/0317840 A1 Dec. 16, 2010

(51) Int. Cl.
C07H 21/04 (2006.01)
(52) U.S. Cl. .................. 536/24.5; 536/24.31; 536/24.1; 514/44; 435/6; 435/325; 435/375
(58) Field of Classification Search ........................ None
See application file for complete search history.

(56) References Cited

PUBLICATIONS

Ng et al. hnRNP K as a target to suppress HBV. Plos Medicine vol. 2, Jul. 2005: 0673-0683.*
Beate Fredrich et al, "Induction of anti-proliferative mechanisms in hepatitis B virus producing cells", Journal of Hepatology, Feb. 2005; vol. 43, pp. 696-703.
Irene Pino, Ruben Pio, Gemma Toledo, Natalia Zabalegui, Silvestre Vicent, Natalia Rey, Maria D. Lozano, Wenceslao Torree, Jesu's Garcia'a-Foncillasd, Luis M. Montuenga, "Altered patterns of expression of members of the heterogeneous nuclear ribonucleoprotein (hnRNP) family in lung cancer". p. 131-143 Lung Cancer (2003).
Ryuji Ikeda, Xiao-Fang Che, mina Ushiyama, Tatsuya Yamaguchi, Hiroshi Okumura, Yuichi Nakajima, Yasuo Takeda, Yoshihiko Shibayama, Ttsuhiko Furukawa, Masatatsu Yamamoto, Misako Haraguchi, Tomoyuki Sumizawad, Katsushi Yamada, Shin-Ichi Akiyama, "2-Deoxy-D-ribose inhibits hypoxia-induced apoptosis by suppressing the phosphorylation of p38 MAPK" p. 280-285, Biochemical and Biophysical Research Communications 342 (2006).
P Roychoudhury and K Chaudhuri "Evidence for heterogeneous nuclear ribonucleoprotein K overexpression in oral squamous cell carcinoma" British Journal of Cancer (2007) 97, p. 574-575.

Karol Bomsztyk, Oleg Denisenko, and Jerzy Ostrowskii, "hnRNP K: One protein multiple processes" Bio Essays 26 p. 629-638, 2004.
Masaki Kitazono, Yuji Takebayashi, Kenji Ishitsuka, Sonshin Takao, Ayako Tani, Tatsuhiko Furukawa, Kazutaka Miyadera, Yuji Yamada, Takashi Aikou, and Shin-Ichi Akiyama, "Prevention of Hypoxia-Induced Apoptosis by the Angiogenic Factor Thymidine Phosphorylase." Biochemical and Biophysical Research Communications 253, p. 797-803(1998).
B Carpenter, M McKay, SR Dundas, LC Lawrie, C Telferr and GI Murray "Heterogeneous nuclear ribonucleoprotein K is over expressed, aberrantly localized and is associated with poor prognosis in colorectal cancer." British Journal of Cancer (2006)95, p. 921-927.
Sandra Liekensa, Annelies Bronckaers, Maria-Je'Sus Pe'Rez-Pe'Rez, Jan Balzarini, "Targeting platelet-derived endothelial cell growth factor/thymidine phosphorylase for cancer therapy" Biochemical Pharmacology 74 (2007) p. 1555-1567.
Hiromitsu Hatakeyama, Tadishi Kondo, Kiyonaga Fujii, Yukihiro Nakanishi, Hoichi Kato, Satoshi Fukuda and Setsuo Hirohashi "Protein clusters associated with carcinogenesis, histological differentiation and nodal metastasis in esophageal cancer" Proteomics 2006, 6, p. 6300-6316.
Lih-Chyang Chen, Chuen Hsueh, Ngan-Ming Tsang, Ying Liang, Kai-Ping Chang, Sheng-Po Hao, Jau-Song Yu, and Yu-Sun Chang, Heterogeneous Ribonucleoprotein K and Thymidine Phosphorylase Are Independent Prognostic and Therapeutic Makers for Nasopharyngeal Carcinoma, Published: Jun. 15, 2008, pp. 3807-3813.
Lih-Chyang Chen, Chuen Hsueh, Ngan-Ming Tsang, Ying Liang, Sheng-Po Hao, Jau-Song Yu, and Yu-Sun Chang, Heterogeneous Nuclear Ribonucleoprotein K and Thymidine Phosphorylase Are Independent Prognostic and Therapeutic Makers for Nasopharyngeal Carcinoma, Published Nov. 7, 2008.
Lih-Chyang Chen, Chuen Hsueh, and Yu-Sun Chang, Mechanistic Study for Interleukin-8 Regulation in Immune Cell-Infiltrated Nasopharyngeal Carcinoma, Published: Mar. 29, 2009.
L-C Chen, H-P Liu, H-P Li, C. Hsueh, J-S Yu, C-L Liang and Y-S Chang, Thymidine Phosphorylase MRNA Stability and Protein Levels Are Increased through ERKk-mediated Cytoplamic Accumulation of hnRNP K in Nasopharyngeal Carciinoma Cells, Published: Mar. 30, 2009, pp. 1904-1915.

* cited by examiner

*Primary Examiner* — Kimberly Chong
(74) *Attorney, Agent, or Firm* — Muncy, Geissler, Olds & Lowe, PLLC

(57) ABSTRACT

The present invention discloses an hnRNP K expression-inhibiting compound and a siRNA sequence thereof, wherein a siRNA sequence partially or completely complementary to the sequence of hnRNP K is used to inhibit hnRNP K expression, whereby is effectively reduced the survival rate of cancer cells in an anoxic environment.

5 Claims, 3 Drawing Sheets

SEQUENCE LISTING

<160> NUMBER OF SEQ ID NOS: 5

<210> SEQ ID NO 1
<211> LENGTH: 21
<212> TYPE: RNA
<213> ORGANISM: Artificial Sequence
<220> FEATURE:
<223> OTHER INFORMATION: Synthetic hnRNP K-inhibiting siRNA

<400> SEQUENCE: 1
uaaacgcccu gcagaagauu u                                        21

<210> SEQ ID NO 2
<211> LENGTH: 21
<212> TYPE: RNA
<213> ORGANISM: Artificial Sequence
<220> FEATURE:
<223> OTHER INFORMATION: Synthetic hnRNP K-inhibiting siRNA

<400> SEQUENCE: 2
ggucguggcu cauauggugu u                                        21

<210> SEQ ID NO 3
<211> LENGTH: 21
<212> TYPE: RNA
<213> ORGANISM: Artificial Sequence
<220> FEATURE:
<223> OTHER INFORMATION: Synthetic hnRNP K-inhibiting siRNA

<400> SEQUENCE: 3
ugacagaguu guucuuauuu u                                        21

<210> SEQ ID NO 4
<211> LENGTH: 21
<212> TYPE: RNA
<213> ORGANISM: Artificial Sequence
<220> FEATURE:
<223> OTHER INFORMATION: Synthetic hnRNP K-inhibiting siRNA

<400> SEQUENCE: 4
gcaagaauau uaaggcucuu u                                        21

<210> SEQ ID NO 5
<211> LENGTH: 2995
<212> TYPE: DNA
<213> ORGANISM: Artificial Sequence
<220> FEATURE:
<223> OTHER INFORMATION: Chemically synthesized mRNA of hnRNP K

<400> SEQUENCE: 5
ccctagccgc cctccccccc agctagtgag tgcgcgaacg agaaaggagg agggcgctcc    60
aggcgacagc actgcagacg ccattatcct ctgtttctct gctgcaccga cctcgacgtc   120
ttgcctgtgt cccacttgtt cgcggcctat aggctactgc agcactgggg tgtcagttgt   180
tggtccgacc cagaacgctt cagttctgct ctgcaaggat atataataac tgattggtgt   240
gcccgtttaa taaagaata tggaaactga acagccagaa gaaaccttcc ctaacactga   300

```
aaccaatggt gaatttggta aacgccctgc agaagatatg gaagaggaac aagcatttaa      360
aagatctaga aacactgatg agatggttga attacgcatt ctgcttcaga gcaagaatgc      420
tggggcagtg attggaaaag gaggcaagaa tattaaggct ctccgtacag actacaatgc      480
cagtgtttca gtcccagaca gcagtggccc cgagcgcata ttgagtatca gtgctgatat      540
tgaaacaatt ggagaaattc tgaagaaaat catccctacc ttggaagagg cctgcagtt       600
gccatcaccc actgcaacca gccagctccc gctcgaatct gatgctgtgg aatgcttaaa      660
ttaccaacac tataaaggaa gtgactttga ctgcgagttg aggctgttga ttcatcagag      720
tctagcagga ggaattattg gggtcaaagg tgctaaaatc aaagaacttc gagagaacac      780
tcaaaccacc atcaagcttt tccaggaatg ctgtcctcat ccactgaca gagttgttct       840
tattggagga aacccgata gggttgtaga gtgcataaag atcatccttg atcttatatc       900
tgagtctccc atcaaaggac gtgcacagcc ttatgatccc aattttacg atgaaaccta       960
tgattatggt ggttttacaa tgatgtttga tgaccgtcgc ggacgccag tgggatttcc      1020
catgcgggga agaggtggtt ttgacagaat gcctcctggt cggggtgggc gtcccatgcc     1080
tccatctaga agagattatg atgatatgag ccctcgtcga ggaccacctc cccctcctcc     1140
cggacgaggc ggccggggtg gtagcagagc tcggaatctt cctcttcctc caccaccacc     1200
acctagaggg ggagacctca tggcctatga cagaagaggg agacctggag accgttacga     1260
cggcatggtt ggtttcagtg ctgatgaaac ttgggactct gcaatagata catggagccc     1320
atcagaatgg cagatggctt atgaaccaca gggtggctcc ggatatgatt attcctatgc     1380
aggggggtcgt ggctcatatg gtgatcttgg tggacctatt attactacac aagtaactat     1440
tcccaaagat ttggctggat ctattattgg caaaggtggt cagcggatta acaaatccg      1500
tcatgagtcg ggagcttcga tcaaaattga tgagccttta aaggatccg aagatcggat      1560
cattaccatt acaggaacac aggaccagat acagaatgca cagtatttgc tgcagaacag     1620
tgtgaagcag tatgcagatg ttgaaggatt ctaatgcaag atatttttc tttttttatag     1680
tgtgaagcag tattctggaa agttttccta agactagtga agaactgaag gagtcctgca     1740
tcttttttt tttatctgct ctgttttaaa agccaacat tcctctgctt cataggtgtt       1800
ctgcatttga ggtgtagtga aatctttgct gttcaccaga tgtaatgttt tagttcctta     1860
caaacagggt tgggggggg aagggcgtgc aaaaactaac attgaaattt tgaaacagca      1920
gcagagtgag tggattttat ttttcgttat tgttggtggt ttaaaaaatt ccccccatgt     1980
aattattgtg aacaccttgc tttgtggtca ctgtaacatt tgggggtgg acagggagg       2040
aaaagtaaca atagtccaca tgtccctggc atctgttcag agcagtgtgc agaatgtaat     2100
gctcttttgt aagaaacgtt ttatgatttt taaaataaat ttagtgaacc tattttggt      2160
ggtcattttt ttttttaagac agtcatttta aaatggtggc tgaatttccc aacccacccc    2220
caaactaaac actaagttta attttcagct cctctgttgg acatataagt gcatctcttg     2280
ttggacatag gcaaaataac ttggcaaact tagttctggt gatttcttga tggtttggaa     2340
gtctattgct gggaagaaat tccatcatac atattcatgc ttataataag ctggggattt    2400
tttgtttgtt tttgcaaatg cttgccccta cttttcaaca attttctatg ttagttgtga    2460
agaactaagg tggggagcag tactacaagt tgagtaatgg tatgagtata taccagaatt     2520
ctgattggca gcaagttta ttaatcagaa taacacttgg ttatggaagt gactaatgct      2580
gaaaaaattg attattttta ttagataatt tctcacctat agacttaaac tgtcaatttg     2640
ctctagtgtc ttattagtta aactttgtaa aatatatata tacttgtttt tccattgtat     2700
```

```
gcaaattgaa agaaaaagat gtaccatttc tctgttgtat gttggattat gtaggaaatg    2760
tttgtgtaca attcaaaaaa aaaaaagatg aaaaaagttc ctgtggatgt tttgtgtagt    2820
atcttggcat ttgtattgat agttaaaatt cacttccaaa taaataaaac acccatgatg    2880
ctagatttga tgtgtgcccg atttgaacaa gggttgattg acacctgtaa aatttgttga    2940
aacgttcctc ttaaaaggaa atatagtaat cttatgtaaa aaaaaaaaaa aaaaa         2995
```

US 8,013,144 B2

HNRNP K EXPRESSION-INHIBITING COMPOUND AND SIRNA SEQUENCE THEREOF

FIELD OF THE INVENTION

The present invention relates to an RNA interfering technology, particularly to an hnRNP K expression-inhibiting compound and a siRNA sequence thereof.

DESCRIPTION OF THE RELATED ART

Heterogeneous nuclear ribonucleoprotein K (hnRNP K) is a member of the ribonucleoprotein family. HnRNP K can directly interact with DNA and RNA via the K homology domain and can regulate gene expression in different aspects, including transcription, translation and ligation. HnRNP K may induce canceration via regulating the expression of oncogenes c-myc and eIF4E. HnRNP K can respectively join with the internal ribosome entry site of c-myc and the polypyrimidine of the promoter of eIF4E to induce the expression of c-myc and eIF4E. As hnRNP K normally exists in the nucleus, it cannot undertake regulation and transcription unless it transfers to cytoplasm. A recent paper pointed out that hnRNP K may cause the metastasis of fibrosarcoma cells. Therefore, hnRNP K is a potential target for metastasis therapy. Some clinical researches pointed out that hnRNP K is abnormally expressed in cells of some specified cancers, including colorectal cancer, esophagus cancer, lung cancer, oral squamous cell cancer, and prostate cancer. The reduced hnRNP K expression also correlates with the shorter survival period of the patients of Dukes C colorectal cancer.

The Inventors found that hnRNP K is over-expressed in nasopharyngeal cancer and clinically correlates with the overall survival rate of a patient and the incidence rate of distant metastasis. Therefore, hnRNP K can be used as a biomarker for predicting the malignancy of cancer. In the current cancer therapy technology, there is still none molecular inhibiting method or medicine inhibiting the expression of hnRNP K—the over-expressed gene in colorectal cancer, lung cancer, oral squamous cell cancer, and nasopharyngeal cancer.

SUMMARY OF THE INVENTION

The primary objective of the present invention is to provide an hnRNP K (heterogeneous nuclear ribonucleoprotein K) expression-inhibiting compound and a siRNA (small interfering RNA) sequence thereof, wherein the siRNA corresponding to TP is used to effectively inhibit hnRNP K expression and suppress the growth, metastasis and invasion of cancer.

To achieve the abovementioned objective, the present invention proposes an hnRNP K expression-inhibiting compound and a siRNA sequence thereof, wherein a siRNA is used to inhibit hnRNP K expression, and wherein a small segment of RNA having about 18-24 pieces of nucleotides matches with the mRNA (messenger RNA) of hnRNP K and then the intracellular dicer recognizes the segment of RNA, whereby the mRNA of hnRNP K is cut off, and the hnRNP K expression is inhibited.

The siRNA designed by the present invention matches with hnRNP K mRNA and has a transcribable sequence

| UAAACGCCCUGCAGAAGAUUU | (SEQ ID NO: 1) |
| GGUCGUGGCUCAUAUGGUGUU | (SEQ ID NO: 2) |
| UGACAGAGUUGUUCUUAUUUU | (SEQ ID NO: 3) |
| GCAAGAAUAUUAAGGCUCUUU | (SEQ ID NO: 4) | which can inhibit hnRNP K expression and thus can reduce the survival rate of cancer cells in an anoxic environment.

Below, the present invention is described in detail in cooperation with the attached drawings to make easily understood the objective, characteristics and accomplishments of the present invention.

DETAILED DESCRIPTION OF THE INVENTION

Figure 1A:
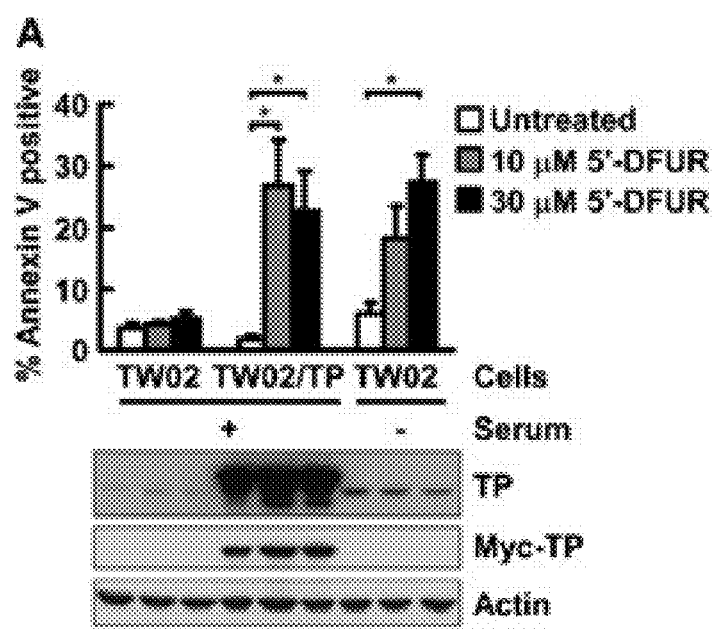
FIGS. 1A and 1B are diagrams respectively schematically showing the influence of the expression of TP, which is the target gene of hnRNP K, on the cell line of nasopharyngeal cancer in a 5'-DFUR environment and an anoxic environment.

The hnRNP K (heterogeneous nuclear ribonucleoprotein K) expression-inhibiting compound and a siRNA (small interfering RNA) sequence thereof can effectively inhibit hnRNP K expression and thus can reduce the survival rate of cancer cells in an anoxic environment and can then suppress the growth of cancer cells, includes colorectal cancer, lung cancer, oral squamous cell cancer, prostate cancer, nasopharyngeal cancer. The nasopharyngeal cancer cells are used as the exemplification of the abovementioned cancer cells in the present invention.

In related experiments, the Inventors found that hnRNP K and the target thereof—TP are over-expressed in nasopharyngeal cancer. The abnormal hnRNP K expression and TP over-expression in cytoplasm correlates with the shorter overall survival period and the higher incidence rate of distant metastasis. A multivariate analysis shows that hnRNP K and TP in cytoplasm are the independent factors for prognosis. Further, TP over-expression in nasopharyngeal cancer cells makes the cancer cells more sensitive to the intermediate product of capecitabine—the precursor medicine 5-fluoro-5'-deoxyuridine (5'-DFUR), which can induce the apoptosis of cancer cells. Besides, the removal of serum will increase the stability of TP and cause TP over-expression.

Furthermore, RT-PCR-based immunoprecipitation and the transfer of hnRNP K from nucleus to cytoplasm shows that a UMP- and CMP-rich segment of TP can directly interact with hnRNP K. Therefore, inhibiting hnRNP K expression can reduce TP expression. It means that hnRNP K should be the upstream of TP. In the reaction mechanism, both the MEK inhibitor (Mitogen-activated protein/Extracellular signal-regulated Kinase) and the amino mutation of p-ERK (phosphorylated Extracellular signal-Regulated kinases) of hnRNP K can reduce hnRNP K expression in cytoplasm. Therefore, the phosphorylation of hnRNP K by ERK maybe plays an important role in inducing TP.

Besides, the TP expression activated by hnRNP K can inhibit the anoxic apoptosis of nasopharyngeal cancer cells. In conclusion, our experiments show that ERK can induce increasing hnRNP K expression. Thus, hnRNP K is the upstream of TP, and TP is the downstream target of hnRNP K. Both hnRNP K and TP are effective indicators to prognose nasopharyngeal cancer and deserves designing new targeted-therapy medicine thereof, which should benefit cancer therapy.

Therefore, the present invention suppresses the growth, metastasis and invasion of nasopharyngeal cancer via inhibiting hnRNP K expression. The hnRNP K expression-inhibiting compound may be the nucleotide-based molecules of RNA or DNA, which has a sense region and an antisense region jointly forming a duplex region. The sense region and the antisense region respectively have a length of 18-30 nucleotides. The antisense region has a sequence completely or partially matching the sequence of the mRNA of hnRNP K, whereby hnRNP K expression is inhibited, and the growth, metastasis, and invasion of cancer cells is suppressed.

In other words, the hnRNP K-inhibiting siRNA contains the following sequence:

```
UAAACGCCCUGCAGAAGAUUU    (SEQ ID NO: 1)
GGUCGUGGCUCAUAUGGUGUU    (SEQ ID NO: 2)
UGACAGAGUUGUUCUUAUUUU    (SEQ ID NO: 3)
GCAAGAAUAUUAAGGCUCUUU    (SEQ ID NO: 4)
```

Below, experimental data is used to prove the efficacies of the present invention. The cell lines of nasopharyngeal cancer NPC-TW01, NPC-TW02 and NPC-TW04 were cultivated in DMEM (Dulbecco's Modified Eagle's Medium) supplemented with 10% fetal bovine serum, 100 U/ml penicillin, and 100 μg/ml streptomycin at a temperature of 37° C. in a humidified 5% $CO_2$ atmosphere. The cells are also cultivated in a serum-free DMEM, i.e. treated with a serum deprivation process. The cell lines NPC-TW02 is cultivated in DMEM supplemented with 10% fetal bovine serum, 100 U/ml penicillin, and 100 μg/ml streptomycin at 37° C. in a humidified 5% $CO_2$ atmosphere. The expression of endogenous TP can be induced by the serum deprivation processing, as shown in FIG. 1A.

Figure 1B:
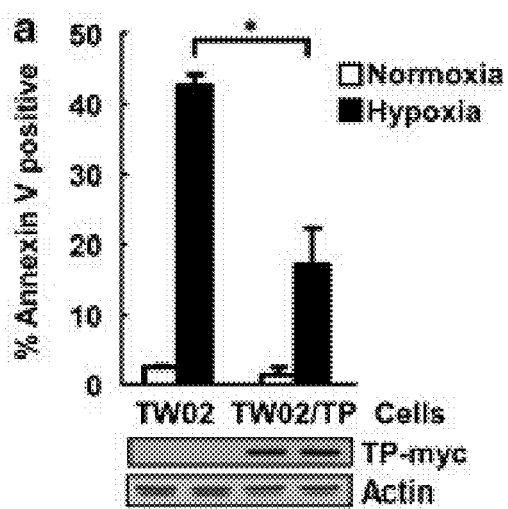

Refer to FIG. 1A and FIG. 1B. A cell line of nasopharyngeal cancer NPC-TW02/TP is established to stably express exogenous TP. First, the TP-expression carrier pcDNA3.1-PT is transfected to the cell line. Next, the cell line is screened and then cultivated in a culture solution having 500 μg/ml G418. Next is performed a cytotoxicity assay, wherein NPC-TW02 and NPC-TW02/TP are respectively processed with 5'-DFUR (a product of Sigma-Aldrich, St. Louis, Mo., USA). Next, the cell lines are further cultivated for 72 hours. Next, the cell membranes are everted to expose phosphatidylserine. Then, phosphatidylserine is analyzed with the Vybrant® Apoptosis Assay Kit #2 (a product of Invitrogen).

Figure 2:
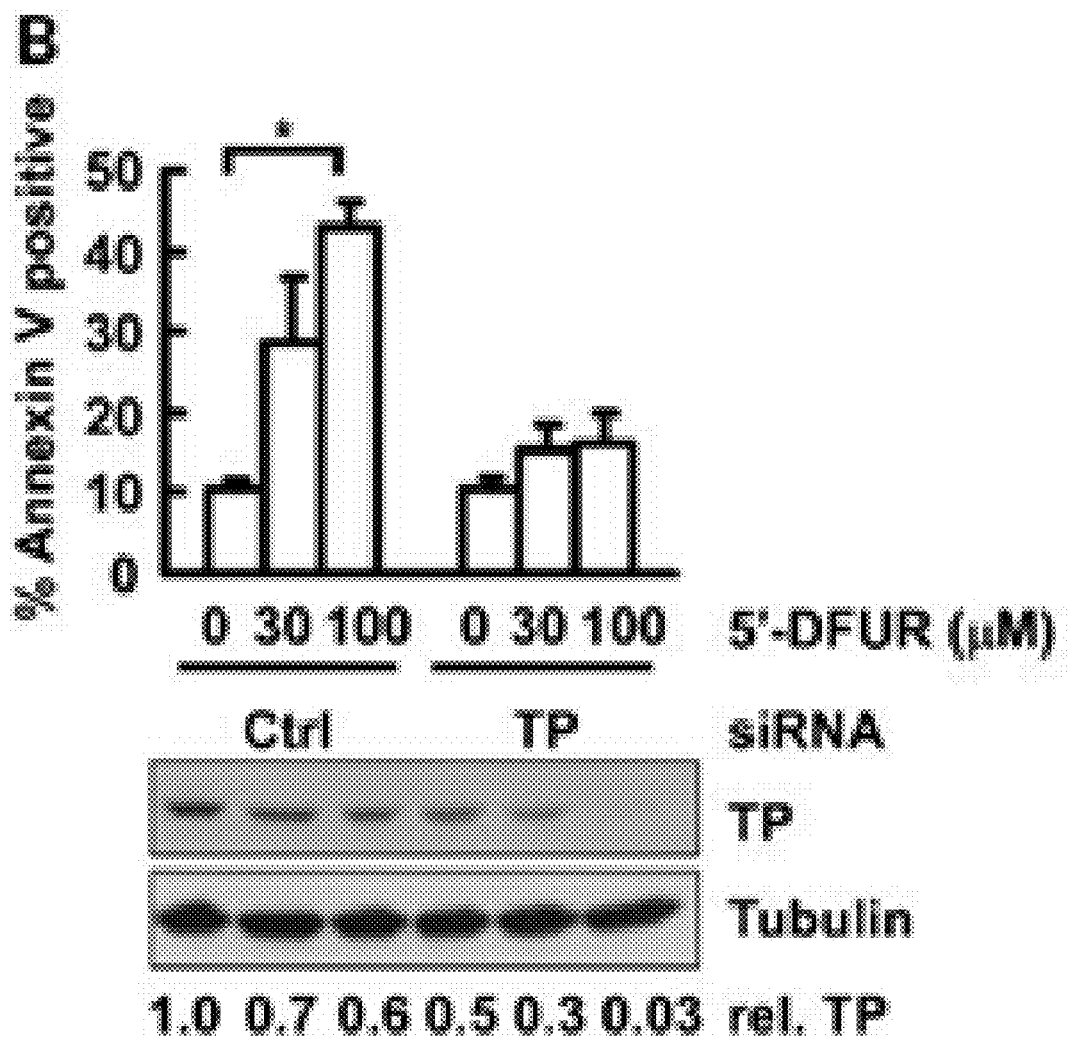
FIG. 2 is a diagram schematically showing the effect of an hnRNP K expression-inhibiting compound according to the present invention.

Firstly, $2 \times 10^5$ cells are taken out and washed with PBS. Next, a buffer solution (10 mM HEPES, 140 mM NaCl, 2.5 mM $CaCl_2$, pH 7.4) is used to adjust the solution to have a cell concentration of $2 \times 10^6$/mL. Next, 5 μl Alexa Fluor® 488 annexin V is added into 1000 cell suspension, and then the cell suspension reacts at an ambient temperature for 15 minutes. Next, the cell specimens (10000 events) are analyzed with a flow cytometer (a product of Becton Dickinson), as shown in FIG. 3. Next is performed an anoxic experiment, wherein a six-hole culture tray planted with cells is placed in a modular incubator chamber (a product of Billus-Rothenberg, Del Mar, Calif.), and an air having 2% $O_2$, 5% $CO_2$, and 93% $N_2$ flows through the incubator chamber with a flow rate of 20 l/min for 8 minutes. Next, the incubator chamber is sealed, and the cells are cultivated for 72 hours at a temperature of 37° C. Refer to FIG. 2. Next, the cell membranes are everted to expose phosphatidylserine. Then, phosphatidylserine is analyzed with the Vybrant® Apoptosis Assay Kit #2 (a product of Invitrogen).

Figure 3A:
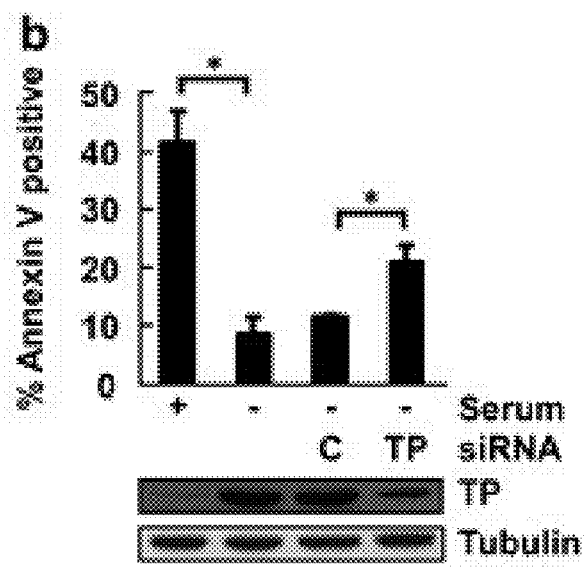
FIGS. 3A and 3B are diagrams schematically showing the effect of an hnRNP K expression-inhibiting compound according to the present invention.
Figure 3B:
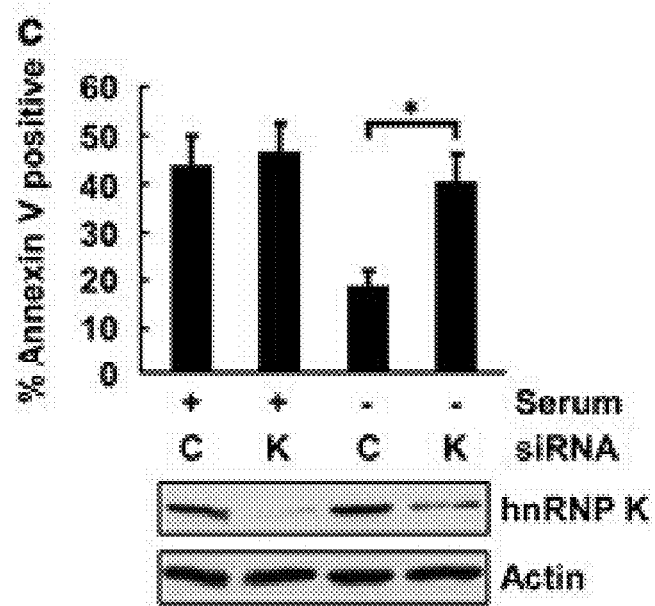

According to the operation manual, 50 μg transfection agent TransIT-TKO (a product of Mints Bio Corporation) is used to transfect 50 nmol/l dsRNA duplexes to the cell line NPC-TW02, wherein a 21-bp hnRNP K and TP-addressing RNA duplex (SMARTpool reagents, Dharmacon, Lafayette, Colo.) and a 21-bp none-addressing RNA duplex (Research Biolabs Ayer Rajah Industrial Estate) are transfected to the cell line NPC-TW02. 24 hours later from transfection, the siRNA-containing culture solution is replaced with a serum-containing culture solution and a serum-free culture solution. Refer to FIG. 2, FIG. 3A and FIG. 3B. 48 hours later from culture solution replacement, the cells are collected to extract cell protein to examine the gene expression-inhibiting effect of the transfected RNA duplexes.

The mRNA of hnRNP K may have a sequence shown in Table. 1. (SEQ ID NO: 5)

TABLE 1

```
  1 ccctagccgc ccctccccc agctagtgag tgcgcgaacg agaaaggagg agggcgctcc 61 aggcgacagc actgcagacg ccattatcct ctgtttctct gctgcaccga cctcgacgtc 121 ttgcctgtgt cccacttgtt cgcggcctat aggctactgc agcactgggg tgtcagttgt 181 tggtccgacc cagaacgctt cagttctgct ctgcaaggat atataataac tgattggtgt 241 gcccgtttaa taaaagaata tggaaactga acagccagaa gaaaccttcc ctaacactga 301 aaccaatggt gaatttggta aacgccctgc agaagatatg gaagaggaac aagcatttaa 361 aagatctaga aacactgatg agatggttga attacgcatt ctgcttcaga gcaagaatgc 421 tggggcagtg attggaaaag gaggcaagaa tattaaggct ctccgtacag actacaatgc 481 cagtgtttca gtcccagaca gcagtggccc cgagcgcata ttgagtatca gtgctgatat 541 tgaaacaatt ggagaaattc tgaagaaaat catccctacc ttggaagagg gcctgcagtt 601 gccatcaccc actgcaacca gccagctccc gctcgaatct gatgctgtgg aatgcttaaa 661 ttaccaacac tataaaggaa gtgactttga ctgcgagttg aggctgttga ttcatcagag
```

TABLE 1-continued

```
 721 tctagcagga ggaattattg gggtcaaagg tgctaaaatc aaagaacttc gagagaacac
 781 tcaaaccacc atcaagcttt tccaggaatg ctgtcctcat tccactgaca gagttgttct
 841 tattggagga aaacccgata gggttgtaga gtgcataaag atcatccttg atcttatatc
 901 tgagtctccc atcaaaggac gtgcacagcc ttatgatccc aattttttacg atgaaaccta
 961 tgattatggt ggttttacaa tgatgtttga tgaccgtcgc ggacgcccag tgggatttcc
1021 catgcgggga gaggtggtt ttgacagaat gcctcctggt cggggtgggc gtcccatgcc
1081 tccatctaga agagattatg atgatatgag ccctcgtcga ggaccacctc cccctcctcc
1141 cggacgaggc ggccggggtg gtagcagagc tcggaatctt cctcttcctc caccaccacc
1201 acctagaggg ggagacctca tggcctatga cagaagaggg agacctggag accgttacga
1261 cggcatggtt ggtttcagtg ctgatgaaac ttgggactct gcaatagata catggagccc
1321 atcagaatgg cagatggctt atgaaccaca gggtggctcc ggatatgatt attcctatgc
1381 aggggggtcgt ggctcatatg gtgatcttgg tggacctatt attactacac aagtaactat
1441 tcccaaagat ttggctggat ctattattgg caaaggtggt cagcggatta aacaaatccg
1501 tcatgagtcg ggagcttcga tcaaaattga tgagcccttta gaaggatccg aagatcggat
1561 cattaccatt acaggaacac aggaccagat acagaatgca cagtatttgc tgcagaacag
1621 tgtgaagcag tatgcagatg ttgaaggatt ctaatgcaag atattttttc ttttttatag
1681 tgtgaagcag tattctggaa agttttctta agactagtga agaactgaag gagtcctgca
1741 tcttttttt tttatctgct tctgtttaaa aagccaacat tcctctgctt cataggtgtt
1801 ctgcatttga ggtgtagtga aatctttgct gttcaccaga tgtaatgttt tagttcctta
1861 caaacagggt tggggggggg aagggcgtgc aaaaactaac attgaaattt tgaaacagca
1921 gcagagtgag tggattttat ttttgcttat tgttggtggt ttaaaaaatt ccccccatgt
1981 aattattgtg aacaccttgc tttgtggtca ctgtaacatt tgggggtgg cagaggagg
2041 aaaagtaaca atagtccaca tgtccctggc atctgttcag agcagtgtgc agaatgtaat
2101 gctcttttgt aagaaacgtt ttatgatttt taaaataaat ttagtgaacc tattttggt
2161 ggtcattttt tttttaagac agtcatttta aaatggtggc tgaatttccc aacccacccc
2221 caaactaaac actaagttta attttcagct cctctgttgg acataaagt gcatctcttg
2281 ttggacatag gcaaaataac ttggcaaact tagttctggt gatttcttga tggtttggaa
2341 gtctattgct gggaagaaat tccatcatac atattcatgc ttataataag ctggggattt
2401 tttgtttgtt tttgcaaatg cttgccccta cttttcaaca attttctatg ttagttgtga
2461 agaactaagg tggggagcag tactacaagt tgagtaatgg tatgagtata taccagaatt
2521 ctgattggca gcaagtttta ttaatcagaa taacacttgg ttatggaagt gactaatgct
2581 gaaaaaattg attattttta ttagataatt tctcacctat agacttaaac tgtcaatttg
2641 ctctagtgtc ttattagtta aactttgtaa aatatatata tacttgtttt tccattgtat
2701 gcaaattgaa agaaaagat gtaccatttc tctgttgtat gttggattat gtaggaaatg
2701 gcaaattgaa agaaaaagat gtaccatttc tctgttgtat gttggattat gtaggaaatg
2761 tttgtgtaca attcaaaaaa aaaaaaaatg aaaaagttc ctgtggatgt tttgtgtagt
2821 atcttggcat ttgtattgat agttaaaatt cacttccaaa taaataaaac acccatgatg
2881 ctagatttga tgtgtgcccg atttgaacaa gggttgattg acacctgtaa aatttgttga
2941 aacgttcctc ttaaaaggaa atatagtaat cttatgtaaa aaaaaaaaa aaaaa
```

In conclusion, the present invention proposes an hnRNP K expression-inhibiting compound and a siRNA sequence thereof, which uses an RNA interfering technology to inhibit hnRNP K expression inside cancer cells and suppress canceration, including the growth, metastasis and invasion of cancer cells.

The present invention has been demonstrated with the embodiments described above. However, they are only to exemplify the present invention but not to limit the scope of the present invention. Any equivalent modification or variation according to the spirit of the present invention is to be also included within the scope of the present invention, which is based on the claims stated below.

What is claimed is:

1. A heterogeneous nuclear ribonucleoprotein K expression-inhibiting compound, which is a nucleotide-based molecule having a sense region and an antisense region jointly forming a duplex region, wherein each of said sense region and said antisense region has a length of 18-30 nucleotides, and wherein said antisense region containing a sequence matching with a sequence of an mRNA of heterogeneous nuclear ribonucleoprotein K and inhibiting expression of heterogeneous nuclear ribonucleoprotein K and suppress growth, metastasis and invasion of cancer cells, wherein a sequence of said sense region is expressed by

```
UAAACGCCCUGCAGAAGAUUU    (SEQ ID NO: 1)
GGUCGUGGCUCAUAUGGUGUU    (SEQ ID NO: 2)
UGACAGAGUUGUUCUUAUUUU    (SEQ ID NO: 3)
GCAAGAAUAUUAAGGCUCUUU    (SEQ ID NO: 4).
```

2. The heterogeneous nuclear ribonucleoprotein K expression-inhibiting compound of claim 1, wherein said cancer cells are selected from the group consisting of colorectal cancer cells, lung cancer cells, oral squamous cell cancer cells, prostate cancer cells, and nasopharyngeal cancer cells.

3. The heterogeneous nuclear ribonucleoprotein K expression-inhibiting compound of claim 1, wherein said nucleotide-based molecule is ribonucleic acid or deoxyribonucleic acid.

4. A heterogeneous nuclear ribonucleoprotein K expression-inhibiting small interfering ribonucleic acid sequence, which is expressed by

```
UAAACGCCCUGCAGAAGAUUU    (SEQ ID NO: 1)
GGUCGUGGCUCAUAUGGUGUU    (SEQ ID NO: 2)
UGACAGAGUUGUUCUUAUUUU    (SEQ ID NO: 3)
GCAAGAAUAUUAAGGCUCUUU    (SEQ ID NO: 4)
``` and which can suppress growth, metastasis and invasion of cancer cells via inhibiting expression of heterogeneous nuclear ribonucleoprotein K.

5. The heterogeneous nuclear ribonucleoprotein K expression-inhibiting small interfering ribonucleic acid sequence of claim 4, wherein said cancer cells are selected from the group consisting of colorectal cancer cells, lung cancer cells, oral squamous cell cancer cells, prostate cancer cells, and nasopharyngeal cancer cells.

* * * * *